(12) United States Patent
Paradis

(10) Patent No.: US 6,491,668 B1
(45) Date of Patent: Dec. 10, 2002

(54) NEEDLELESS FLUID TRANSFER

(76) Inventor: Joseph R. Paradis, P.O. Box 22238, Hilton Head Island, SC (US) 29925

( * ) Notice: Subject to any disclaimer, the term of this patent is extended or adjusted under 35 U.S.C. 154(b) by 0 days.

(21) Appl. No.: 09/204,784

(22) Filed: Dec. 3, 1998

(51) Int. Cl.[7] .................................................. A61M 5/00
(52) U.S. Cl. ..................................................... 604/246
(58) Field of Search .......................... 604/83, 246–247, 604/256–257, 905, 284; 137/903; 251/149.6, 149.7

(56) References Cited

U.S. PATENT DOCUMENTS

| | | | |
|---|---|---|---|
| 5,057,093 A | * 10/1991 | Clegg et al. | |
| 5,242,432 A | * 9/1993 | DeFrank | 604/284 |
| 5,284,475 A | * 2/1994 | Mackal | 604/247 |
| 5,295,658 A | * 3/1994 | Atkinson et al. | |
| 5,390,898 A | * 2/1995 | Smedley et al. | |
| 5,439,451 A | * 8/1995 | Collinson et al. | 604/247 |
| 5,676,346 A | * 10/1997 | Leinsing | |
| 5,699,821 A | * 12/1997 | Paradis | |
| 5,782,816 A | * 7/1998 | Werschmidt et al. | 604/256 |

* cited by examiner

Primary Examiner—Brian L. Casler
Assistant Examiner—LoAn H. Thanh
(74) Attorney, Agent, or Firm—George E. Kersey

(57) ABSTRACT

A valve connector adapted to facilitate fluid access between components is formed by a housing having a through channel. An elastomeric support secured to the housing biases a valve element or plug in the channel into sealing engagement with the support. When a fitting is inserted to depress the plug, it stretches the support and opens a passage through the channel, for example by canting the plug. When the fitting is removed, the stretched support contracts and returns the plug to its position of sealing engagement where the plug, support and housing are swabbable to eliminate pathogens that could otherwise enter the channel when the plug is depressed to open the channel and permit fluid flow therethrough.

16 Claims, 6 Drawing Sheets

Fig. 6A

VALVE CLOSED

Fig. 6B

VALVE OPENED

NEEDLELESS FLUID TRANSFER

Background of the Invention

This invention relates to needleless fluid transfer and, more particularly, to valves and other connectors for introducing and removing fluids with respect to a patient.

When entry is needed into the vascular system of a patient, an intravenous tubing set is commonly used with a primary needle or catheter that accesses the vascular system, and a connector valve is coupled to the needle through tubing for repeated use of a medication delivery system, including a syringe. With such a tubing set, the trauma to the patient is reduced to a single puncture of the vascular system by the primary needle.

Repeated use of the syringe for introducing fluids into the Valve connector does not result in additional patient trauma. In some cases, the connector forms an injection site, an adapter, or extension set for medication added to a constant flow of intravenous solutions through the connector. The intravenous solution flows from an elevated container through the connector into the primary needle or catheter, and medications are typically added to the intravenous solution at the connector.

The valve connectors generally include a sealed entry port which communicates through the tubing and the primary needle into the vascular system of the patient. This sealed entry port is typically constructed of a latex plug sometimes referred to as a septum. Medication is introduced into the connector by penetrating the septum with the secondary needle. The latex septum is self-sealing such that the needle hole created in the septum automatically closes when the secondary needle is removed.

A major drawback of conventional practice is associated with the use of a secondary needle to puncture the septum. Once a needle is exposed to the body fluids of a patient, within a short distance from the insertion site, the injection is considered high risk, and the contaminated needle threatens the health care workers with disease and other life-threatening injuries.

Several devices have been developed which provide for secondary access without the use of the secondary needle. Representative of these devices in the apparatus disclosed in U.S. Pat. No. 5,242,432 issued to DeFrank which discloses a safety valve for introducing medication into a patient. Although such devices may eliminate the risk of secondary needle stick, they present other risks which relate to the pooling of fluid on or around external surfaces. ideally, a connector or other access device should not promote pooling during the ordinary course of its use due to potential for bacterial infection. If a reservoir or cavity is created and not cleaned, bacteria may develop in the reservoir. That bacteria could find its way into the patient's bloodstream while either administering fluids to the patient or removing the fluids from the patient.

In U.S. Pat. No. 5,782,816 which issued to Werschmidt et al. on Jul. 21, 1998 for Bi-directional Valve and Method, the disposable needleless access device is adaptable for use in various medical procedures. Although this device can eliminate the need for a secondary needle, it has a housing with an axis extending between a proximal end and a distal end, with a valve element in the housing movable to form a curved axis by insertion of a male Luer fitting into the proximal end of the housing.

Injection sites used with a blunt cannula have the advantage that the cannula will not pierce the skin of a user, but the preslit injection site has to reseal with enough force that fluids do not ooze outwardly and not allow airborne particulate matter, bacterial or viral, to enter.

Hence, there continues to be a need for an injection site which can be used with a variety of solutions and over a range of fluid pressures. Further, there continues to be a need for such an injection site which will reliably reseal even after many insertions of a blunt cannula.

If intended to be reusable, the injection site should be able to receive a large number of insertions of the cannula without displaying reseal failure. Such an injection site should provide for alignment of the cannula on insertion to result in less chance of damage to the injection site after repeated insertion.

Further, the injection site should be usable with a blunt cannula with a reasonable level of insertion force that will permit health care personnel to readily insert the cannula, but yet not have the cannula easily displaced after insertion.

Accordingly it is an object of the invention to achieve the foregoing advantages without the need for a displaceable plug that adopts axis curvature in order to permit fluid flow.

SUMMARY OF THE INVENTION

In accomplishing the foregoing and related objects, the invention provides a needleless valve connector formed by a housing having an axis extending between a proximal end and a distal end, with a fixed elastomeric support at the proximal end and containing a valve seat against which is disposed a valve element or plug within the housing. The valve element is movable away from the valve seat by a fitting inserted into the proximal end of the housing.

In accordance with one aspect of the invention a side housing communicates with the housing axis beyond the position of maximum movement of the valve element or plug.

The housing and the fixed elastomeric support have a wipable surface at the proximal end, and the valve element has a wipable surface at the proximal end when it is disposed in the housing against the valve seat.

The valve element has a symmetrical axis which is maintained when a force is directed thereagainst, and the valve element can cant or tilt from its initial position to a final position when a force is directed thereagainst.

The valve element has an axis aligned with that of the housing and the elastomeric support when the valve element is positioned against the valve seat, but the axis of the valve element forms an acute angle with the axis of the housing when the valve element or plug is depressed.

In accordance with another aspect of the the invention the proximal end of the housing overlaps the proximal end of the stretchable elastomeric support, and the support is longitudinally grooved to receive longitudinal ribs or flutings of the plug to provide flow channels between the plug and the interior wall of the housing.

In a method of the invention for operating a needless valve the steps include: (a) engaging a plug positioned against an elastomeric support at a proximal end of a housing; and (b) depressing the plug against the support away from a valve seat therein while extending the elastomeric support.

The method includes disposing the plug in the housing against the valve seat; and moving the plug away from the valve seat by insertion of a fitting into the proximal end of the housing, which has a wipable surface at its proximal end. The valve element or plug also has a wipable surface when it is disposed in the housing against the valve seat, so that the entire proximal end of the valve connector is wipable by disinfectant before use in order to assure the elimination of pathogens.

The valve element has a symmetrical axis which is maintained when a force is directed against the valve element, and the proximal end of the housing overlaps the proximal ends of the support.

In a method of the invention for manufacturing a needless valve the steps include: (a) positioning an elastomeric support member at a proximal end of housing; and (b) positioning a plug against a seat in the support. The support is longitudinally slotted, and the plug is longitudinally ribbed, with the ribs forming flutings. The distal end of the housing can include an interior inclined ramp therein.

BRIEF DESCRIPTION OF THE DRAWINGS

Various other features, advantages and characteristics of the invention will become apparent after considering several illustrative embodiments, taken in conjunction with the drawings, in which.

DESCRIPTION OF PREFERRED EMBODIMENTS AND BEST MODE

Figure 1A:
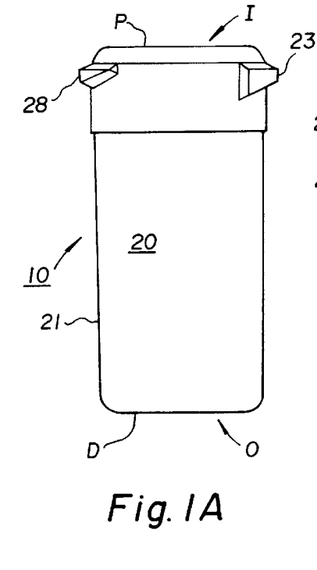
FIG. 1A is a plan view of a valve in accordance with the invention.
Figure 1B:
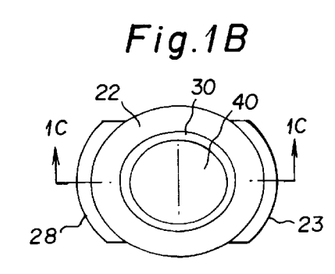
FIG. 1B is a top view of the valve of FIG. 1A.

With reference to the drawings, a valve connector 10 of the invention is shown in FIG. 1A. The valve connector 10 can form part of an intravenous tubing set (not shown), with a length of tubing terminated by a primary needle or catheter that can be inserted into a patient (not shown). The tubing can be connected at the lower portion of wall 21 in FIGS. 1A, 1C and 1E, and extend to the catheter. The inlet I of valve connector 10 can be accessed by the Luer end of a syringe or a fluid container with a male Luer fitment for the flow of fluids and medications into a patient.

Repeated injections or withdrawals of fluids can be accomplished with multiple needle sticks directly into a patient. However, each needle stick is accompanied by trauma. The tubing set including the valve connector 10 reduces trauma by requiring only a single stick into a patient at the position of a primary needle or catheter. The remaining accesses can be made through the connector valve 10, which extends to the catheter through tubing.

Figures 6A, 6B:
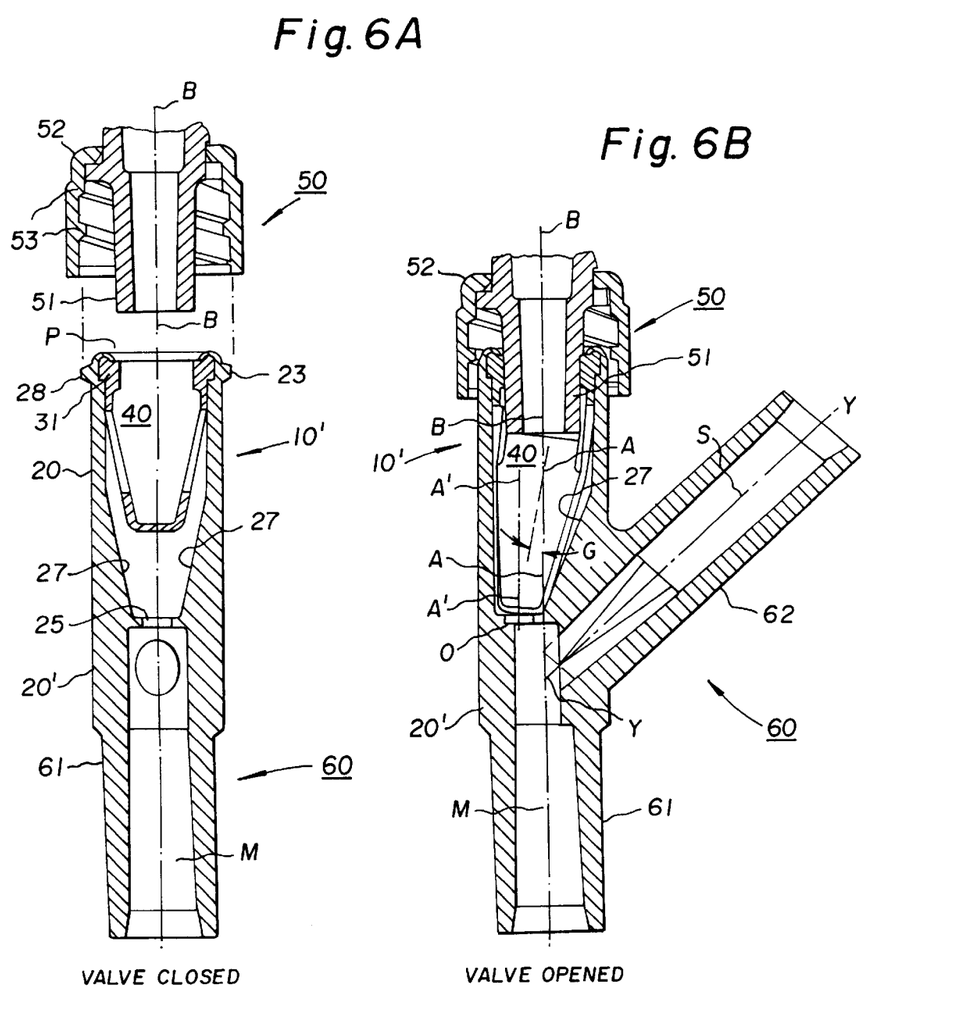
FIG. 6A is a sectional view of a Y-site valve of the invention before operation by an associated Luer fitting.
FIG. 6B is a sectional view of the valve of FIG. 6A during operation by the Luer fitting.

In some cases, the valve connector 10 is adapted to form a "T"-site, or, as illustrated in FIG. 6B and discussed below, a "y"-site. In such cases, the connector 10 is coupled to tubing which communicates with an elevated bottle containing various solutions. As a saline solution or medication from the bottle continuously drips into tubing extending to the connector 10, it can flow through and out of the connector 10. Additional medications can be inserted through a secondary channel in the connector 60 of FIG. 6B, as discussed below.

Thus, the connector of the invention can function as a single or multiple access site.

In a preferred embodiment, the connector 10, as illustrated in FIGS. 1A through 1F includes a housing 20, a stretchable support 30, and a plug 40, all of which extend generally along an interior axis A—A of the connector 10.

The housing 20 is elongated and includes a wall 21 which extends between a proximal end P and a distal end D. At the proximal end P, the wall 21 narrows to form a circular clamp 22. The upper portion of the wall 21 below the clamp 22 has external threads 22 and 23 which form, in a preferred embodiment, a coupling for a Luer fitting as described below in conjunction with FIGS. 2A through 2C.

The wall 21 of the housing 20 has an inner surface 24 bounding channel C that extends through the housing 20 to a distal opening 25 having an axis A'—A' which is offset from the axis A—A. At the proximal end P, the inner surface 24 forms an annular recess 26 which functions as a fixed seat for the support 30.

In proximity to the distal end D, the inner surface 24 forms a ramp 27, illustratively having a partial frusto-conical curvature, which can act in conjunction with displacement of the plug 40 as described below. One or more longitudinal slots (not shown) can be formed in the surface 24 to define auxiliary channels.

Figure 1C:
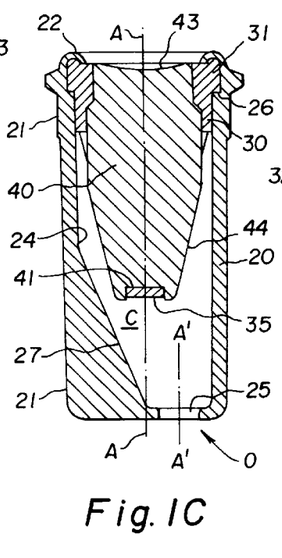
FIG. 1C is a sectional view of the valve of FIG. 1A taken along the lines 1C—1C of FIG. 1B.
Figure 1D:
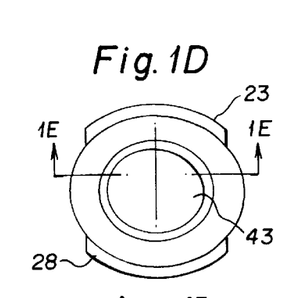
FIG. 1D is a top view of the valve of FIG. 1A rotated through 90 degrees.

The support 30 which is clamped to the housing 20 can be provided in a variety of forms as described in greater detail below. In the embodiment of FIG. 1C, the support 30 is formed as a cylindrical ring 31 to which are connected a plurality of bands 32, of which only bands 32-1 and 32-4 are visible in FIG. 1E. The bands 32-1 and 32-4 are connected at the tip 35 at end 41 of of the plug 40, which has a shoulder 42 positioned against a seat 33 of the support 30.

In addition, the plug 40, which may be of any suitable material including elastomeric, plastic or metallic, has a concave proximal depression 43 and a frusto-conical distal end 44.

Figure 2A:
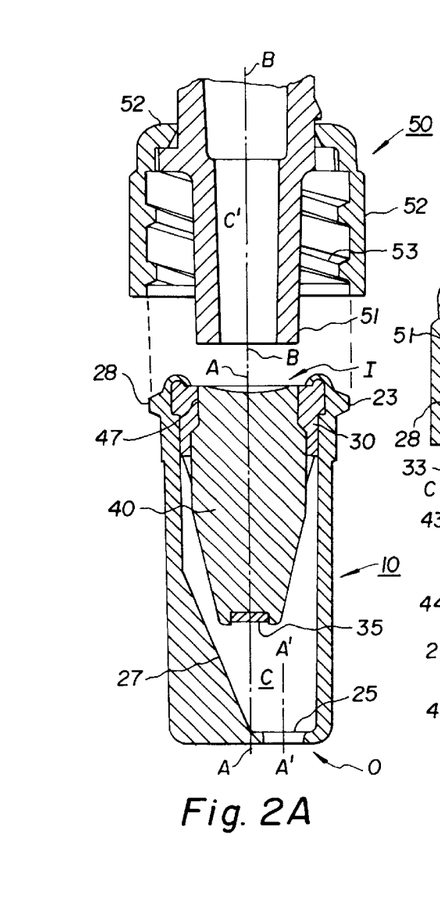
FIG. 2A is a sectional view of the valve of FIG. 1A before operation by an associated Luer fitting.
Figure 2B:
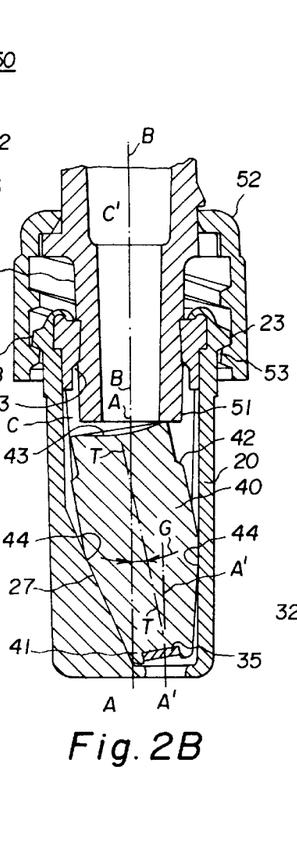
FIG. 2B is a sectional view corresponding to FIG. 2A and the valve of FIG. 1A during operation by a Luer fitting.
Figure 2C:
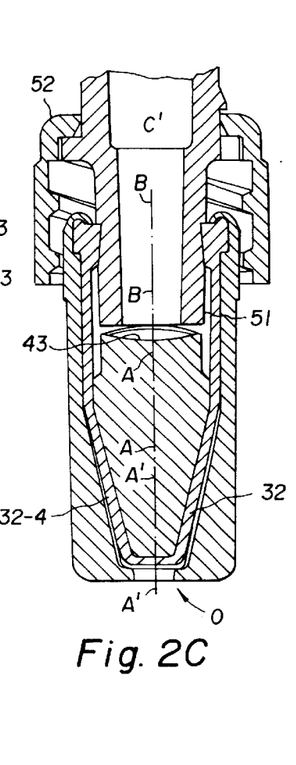
FIG. 2C is a sectional view of the valve of FIG. 1E during operation by the Luer fitting.

One mode of operation of the valve 10 is illustrated in FIGS. 2A through 2C. FIG. 2A is a side view section of the valve 10 before operation by an associated Luer fitting 50 which includes a tip 51 surrounded by a shell 52 containing Luer threads 53. The tip 51 encloses a channel C' of an axis B—B.

As shown in FIG. 2A, the axis B—B of the Luer fitting 50 is aligned with the axis A—A of the connector 10.

To operate the valve 10, the shell 52 is threaded upon the complementary Luer threads 28 and 23 of the connector 10 as indicated in FIG. 2B. This action forces the plug 40 away from the seat 33 of the support 30 causing the shoulder 42 to move downwardly into the channel C. This displacement of the plug 40 permits fluid transfer between the channels C and C' to and from the outlet O. In order to facilitate the outward or inward flow of fluid in the channels C and C', the housing 20 includes an inclined ramp 27 in the form of a partial frusto-conical surface 44', against which the taper of the plug 40 becomes contacted, thus tilting the plug 40 so that its tilt axis T—T forms an angle G with the housing axis A—A. This increases the opening between the concave depression 43 of the plug 40 and the tip 51 of the Luer fitting 50.

It will be appreciated that when the plug 40 is in its tilted position as shown in FIGS. 2B and 2C it remains substantially symmetrical with respect to its tilt axis T—T.

Because of the stretchable bands 32 of the elastomeric support 30 surrounding the plug 40, these bands are extended as shown in FIGS. 2B and 2C. When the tip 51 of the Luer fitting 50 is withdrawn, the bands contract and return the plug 40 to its initial, inactivated position shown in FIGS. 1C, 1E and 2A.

Since the stretchable support 30 is of a yieldable material, the neck 47 of the plug 40 can securely engage the interior wall 37 of the support 30.

Figure 1E:
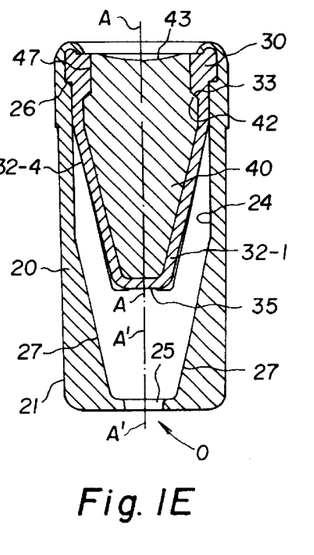
FIG. 1E is a sectional view of the valve of FIG. 1A taken along the lines 1E—1E of FIG. 1D.
Figure 1F:
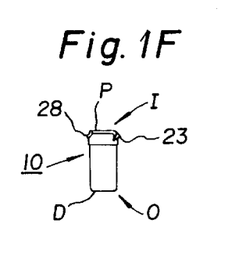
FIG. 1F is a full-scale view of the valve of FIG. 1A.

The housing 20 of FIG. 2B, which shows the valve connector during operation by the Luer fitting, corresponds to the housing 20 of FIG. 1C, shown before activation. Similarly the housing 20 of FIG. 2C, which shows the valve connector during operation corresponds to the housing 20 of FIG. 1E, shown before activation.

Figure 3A:
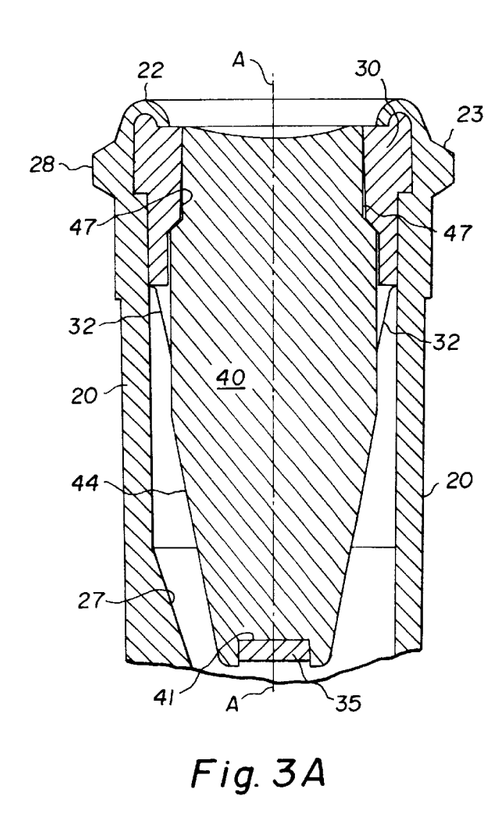
FIG. 3A is an enlarged sectional view of the upper portion of the valve of FIG. 1A before operation by an associated Luer fitting.
Figure 3B:
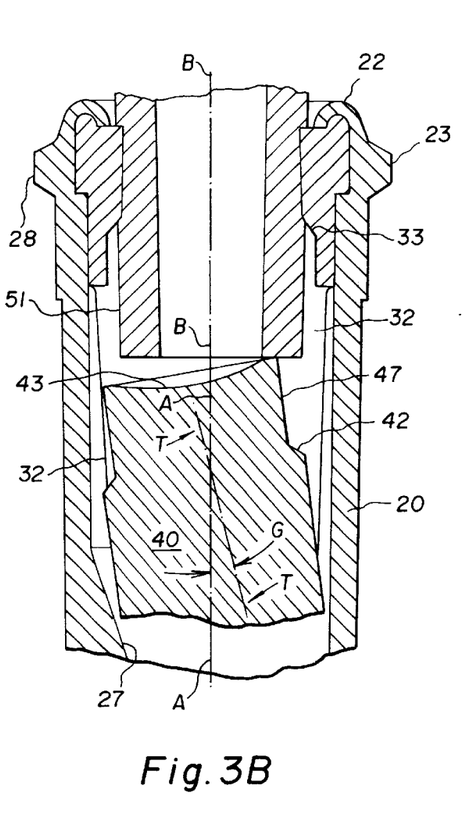
FIG. 3B is an enlarged side view of the upper portion of the valve of FIG. 2B during operation by the Luer fitting.

For further clarification, FIG. 3A is an enlarged sectional view of the upper portion of the valve of FIG. 1C before operation by an associated Luer fitting, and FIG. 3B is an enlarged side view of the upper portion of the valve of FIG. 2B during operation by the Luer fitting.

Figure 4A:
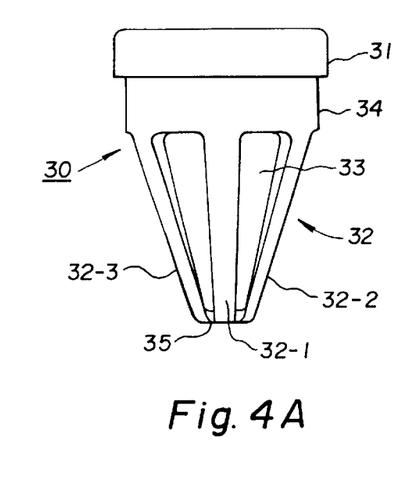
FIG. 4A is a plan view of a support in accordance with the invention for the valve of FIG. 1A.
Figures 4B, 4E:
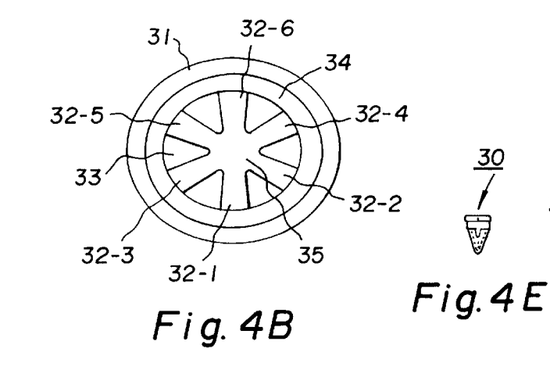
FIG. 4B is a top view of the support of FIG. 4A.
FIG. 4E is a full-scale view of the support of FIG. 4A.
Figure 4C:
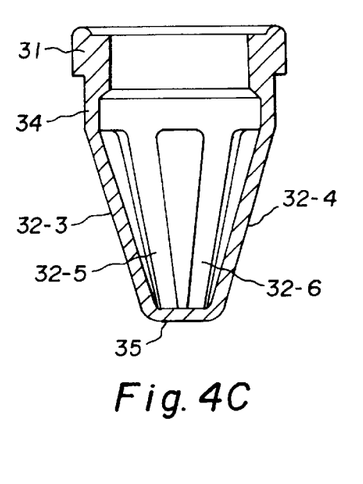
FIG. 4C is a sectional view of the support of FIG. 4A taken along the lines 4C—4C of FIG. 4D.

Details of the support 30 are illustrated in FIGS. 4A through 4C. In the plan view of FIG. 4A, the cylindrical ring 31 overlies a mounting ring 34 for the bands, 32 of which the bands 32-1, 32-2 and 32-3 are visible in FIG. 4A. The remaining bands 32-4, 32-5 and 32-6 are visible in FIG. 4B which is a top view of the support of FIG. 4A.

In addition, as indicated in FIGS. 4A and 4B, longitudinal openings 33 are straddled by adjoining bands 32 and all the bands 32 converge and are joined together at a tip 35.

Figure 4D:
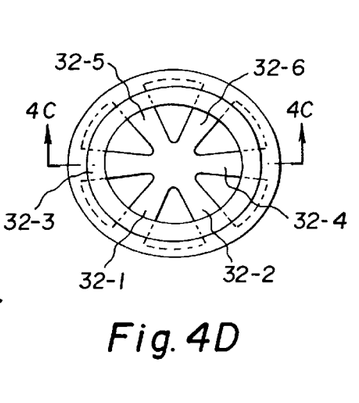
FIG. 4D is a top view of the support of FIG. 4C.

Further details of the support 30 are illustrated in FIG. 4C, which is a cross-sectional view of the support of FIG. 4A taken along the lines 4C—4C of FIG. 4B, and is shown in top view in FIG. 4D.

It will be appreciated that in practice the elastomeric support 30 is miniaturized as shown in FIG. 4E, which is a full-scale view of the support of FIG. 4A.

Figure 5A:
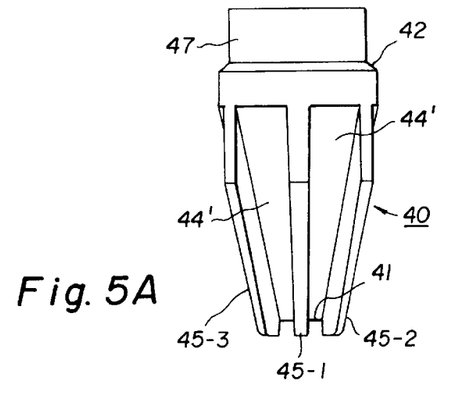
FIG. 5A is a plan view of a plug in accordance with the invention for the valve of FIG. 1A.

Details of the plug 40 are illustrated in FIGS. 5A through 5H. In FIG. 5A, which is a plan view of a plug in accordance with the invention for the valve 10 of FIG. 1A, the plug 40 is shown with longitudinal ribs 45 of which the ribs 45-1, 45-2 and 45-3 are shown in FIG. 5A. The ribs 45 extend from the frusto-conical surface 44 outwardly of the openings 33 in the support 30 when the plug 40 is combined with the support 30 as shown in FIGS. 1A through 2C.

Figure 5B:
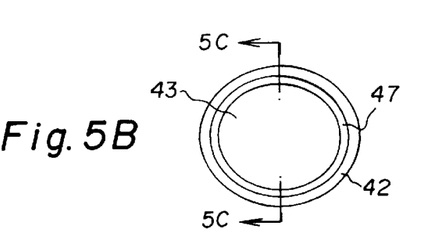
FIG. 5B is a top view of the plug of FIG. 5A.
Figures 5C, 5D, 5E, 5F, 5G:
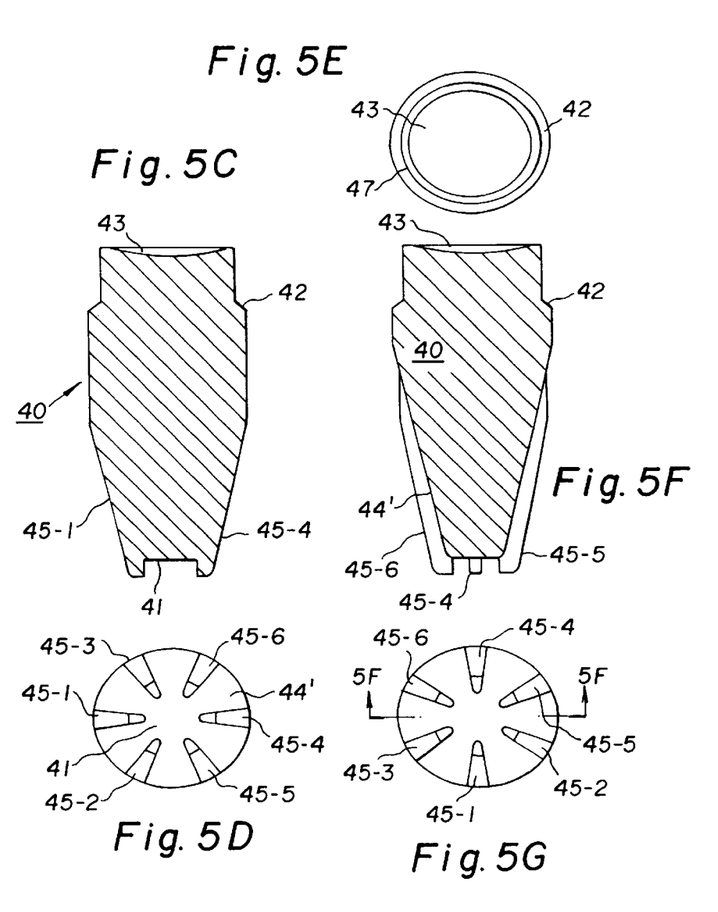
FIG. 5C is a sectional view of the plug of FIG. 5A taken along the lines 5C—5C of FIG. 5B.
FIG. 5D is a bottom view of FIG. 5C.
FIG. 5E is a top view of the valve of FIG. 5A rotated through 90 degrees.
FIG. 5F is a sectional view of the plug of FIG. 5A taken along the lines 5F—5F of FIG. 5G.
FIG. 5G is a bottom view of FIG. 5F.

Other details of the plug 40 are illustrated in FIGS. 5A through 5H. FIG. 5B is a top view of the plug of FIG. 5A while FIG. 5C is a sectional view of the plug of FIG. 5A taken along the lines 5C—5C of FIG. 5B. FIG. 5D is a bottom view of FIG. 5A. FIG. 5E is a top view of the valve of FIG. 5A rotated through 90 degrees, and FIG. 5F is a sectional view of the plug of FIG. 5A taken along the lines 5F—5F of FIG. 5G. FIG. 5G is a bottom view of FIG. 5F.

Figure 5H:
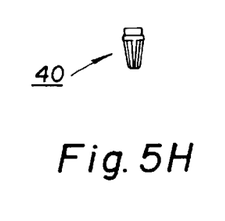
FIG. 5H is a full-scale view of the plug of FIG. 5A.

Corresponding miniaturization for the plug 40, in relation to the support 30 of FIG. 4E, is shown in FIG. 5H, which is a full-scale view of the plug of FIG. 5A.

In order to adapt the invention for multiple site infusion or injection, the valve 10 of FIGS. 1A through 5H is illustratively modified in FIGS. 6A and 6B to form a "Y" site 60. The in-line valve 10' functions in the manner described previously, but the housing 20' is extended to form a main branch 61 which permits the inclusion of a side branch 62.

The side branch 62 includes an axis Y—Y for a channel S that communicates with the main branch channel M below the outlet O of the valve 10'. The side branch 62 can receive a Luer fitting such as a second Luer fitting 50 (not shown if FIG. 6B), or tubing can be inserted in conventional fashion. In addition, the side branch 62 can be modified to have its own valve, such as the valve 10', or a check valve.

FIG. 6A is a sectional view of a Y-site valve 60 of the invention before operation by an associated Luer fitting 50, and FIG. 6B is a sectional view of the valve of FIG. 6A during operation by the Luer fitting 50.

In the foregoing embodiments, the connectors 10 and 60 have been discussed for use with intravenous tubing for accessing the vascular system of a patient. However, the connectors can be used to access other body conduits, such as those associated with the urinary system. In general, the valving of the invention is of applicability wherever control over fluid flow is desirable.

Although the connectors 10 and 60 are operable by male Luer fittings to provide controlled access to tubing sets or any other receptacle, other operating arrangements may be made. In addition, other receptacles may include not only catheters, but also fluid reservoirs or injection manifolds such as those commonly used for the administration of anesthetics.

In general, the connectors 10 and 60 can be used to control the flow of any fluid, either gas or liquid, where automatic self-sealing is desired with controlled access for either unidirectional or bidirectional flow.

It will be appreciated that the foregoing embodiments are merely illustrative and that other variations in form and substance may be made without departing from the spirit and scope of the invention as defined in the appended claims.

What is claimed:
1. A needleless connector valve comprising:
   a housing having an axis extending between a proximal end and a distal end;
   an elastomeric support at said proximal end and containing a valve seat; and a valve element disposed In said elastomeric support against said valve seat;

said valve element being movable away from said valve seat by a fitting inserted into said proximal end of said housing;

wherein said proximal end of said housing overlaps said support and said support is longitudinally grooved.

2. A needleless connector valve as defined in claim 1 wherein said valve element has a symmetrical axis which is maintained when a force is directed thereagainst.

3. A needleless connector valve as defined in claim 2 wherein said valve element cants from its initial position to a final position when a force is directed thereagainst.

4. A needleless connector valve as defined in claim 3 wherein said valve element has an axis aligned with that of said housing when said valve element is positioned against said valve seat.

5. A needleless connector valve as defined in claim 4 wherein the axis of said valve element forms an acute angle with the axis of said housing when said valve element is depressed.

6. A needleless connector valve as defined in claim 1 further including a side housing communicating with said valve beyond the position of maximum movement of said valve element.

7. A needleless connector valve as defined in claim 1 wherein said housing has a wipable surface at said proximal end; and said valve element has a wipable surface when said valve element is disposed in said elastomeric support against said valve seat.

8. The method of operating a needleless valve comprising the steps of:

(a) engaging a plug positioned against an elastomeric support at a proximal end of a housing;

(b) overlapping said proximal end of said housing by said support with longitudinal grooves; and (c) depressing said plug against said support away from a valve seat therein while extending said elastomeric support.

9. The method of claim 8 wherein said plug is disposed in said elastomeric support against said valve seat; and said plug is movable away from said valve seat by insertion of a fitting into the proximal end of said housing.

10. The method of claim 9 wherein said housing at its proximal end has a wipable surface; and said plug has a wipable surface when said valve element is disposed in said elastomeric support against said valve seat.

11. The method of claim 9 wherein said plug has a symmetrical axis which is maintained when a force is directed against said valve element.

12. The method of claim 9 wherein the proximal end of said housing overlaps said support.

13. The method of manufacturing a needless valve comprising the steps of:

(a) positioning an elastomeric support member at a proximal end of a housing having a distal end; and (b) positioning a plug against a seat in said support member; wherein said support member is longitudinally slotted.

14. The method of claim 11 wherein said plug is longitudinally ribbed.

15. The method of claim 14 wherein the ribs of said plug form flutings.

16. The method of claim 11 the distal end of said housing includes an interior inclined frustum cone therein.

* * * * *